United States Patent [19]

Szerlip et al.

[11] Patent Number: 5,364,370
[45] Date of Patent: Nov. 15, 1994

[54] HYPRODERMIC NEEDLE ASSEMBLY WITH SAFETY CAP

[76] Inventors: Gregg M. Szerlip, 224-17 59th Ave., Bayside, N.Y. 11364; Peter J. Wilk, 185 W. End Ave., New York, N.Y. 10023

[21] Appl. No.: 71,503

[22] Filed: Jun. 2, 1993

[51] Int. Cl.⁵ .............................................. A61M 5/32
[52] U.S. Cl. ................................. 604/192; 604/198; 604/263
[58] Field of Search ............... 604/110, 187, 192, 198, 604/263

[56] References Cited

U.S. PATENT DOCUMENTS

| | | | |
|---|---|---|---|
| 4,863,435 | 9/1989 | Sturman et al. | 604/198 |
| 5,049,136 | 9/1991 | Johnson | 604/198 |
| 5,092,851 | 3/1992 | Ragner | 604/192 |

*Primary Examiner*—John D. Yasko
*Attorney, Agent, or Firm*—R. Neil Sudol; Henry D. Coleman

[57] ABSTRACT

A hypodermic device includes a hollow needle having a sharp distal end and a proximal end opposite thereto, a safety cap member provided with an aperture, and a holder or connector coupled to the cap member and the needle for mounting the cap member essentially permanently to the needle so that the cap member covers the distal end of the needle in a storage configuration of the needle and the cap member. The connector member enables a displacement of the cap member relative to the needle so that the distal end of the needle may be extended from the cap member through the aperture. The connector member also serves to return the cap member to the storage configuration relative to the needle upon removal of the distal end of the needle from a skin surface of a patient.

17 Claims, 2 Drawing Sheets

HYPRODERMIC NEEDLE ASSEMBLY WITH SAFETY CAP

BACKGROUND OF THE INVENTION

This invention relates to a hypodermic needle assembly. More particularly, this invention relates to a hypodermic needle assembly with a safety cap. This invention also relates to an associated method for obtaining access to an internal organ of a patient, for example, a blood vessel.

The dangers of hospital and other medical personnel being infected with deadly bacteria and viruses from used hypodermic needles are well documented.

After a hypodermic needle has been used to inject a fluid into or remove a body fluid from a patient, the needle is usually discarded. However, failure to properly dispose of used hypodermic needles has occurred and will inevitably occur, owing to emergencies and other unpredictable circumstances. In such circumstances, there is always the possibility that doctors, nurses, aides, technicians or other personnel will be accidently stuck with used needles. At this time of such deadly and incurable diseases such as acquired immune deficiency syndrome (AIDS), being stuck with a used needle can result in eventual death.

Hypodermic needles are commonly provided with elongate cylindrical caps which are removed prior to hypodermic use. Frequenly, however, such caps are forgotten or misplaced so that the needles are not covered after use.

OBJECTS OF THE INVENTION

An object of the present invention is to provide a means for reducing the chances of hospital personnel becoming inadvertently infected from used hypodermic needles.

Another object of the present invention is to provide a hypodermic needle covering which cannot be misplaced.

An associated objected of the present invention is to provide a hypodermic needle covering which cannot be forgotten.

Yet another object of the present invention is to provide a hypodermic needle covering which is easy to use.

Another, more particular, object of the present invention is to provide a hypodermic needle assembly wherein recovering the needle occurs automatically.

These and other objects of the present invention will be apparent from the drawings and detailed descriptions herein.

SUMMARY OF THE INVENTION

A hypodermic device comprises, in accordance with one conceptualization of the present invention, a hollow needle having a sharp distal end and a proximal end opposite thereto, a safety cap member provided with an aperture, and a holder or connector coupled to the cap member and the needle for mounting the cap member essentially permanently to the needle so that the cap member covers the distal end of the needle in a storage configuration of the needle and the cap member. The connector member enables a displacement of the cap member relative to the needle so that the distal end of the needle may be extended from the cap member through the aperture. The connector member also serves to return the cap member to the storage configuration relative to the needle upon removal of the distal end of the needle from a skin surface of a patient.

According to another feature of the present invention, the connector includes a spring linked at one end to the needle and at an opposite end to the cap member. Preferably, the spring is a helical spring connected to the proximal end of the needle, which extends longitudinally through the spring.

According to a further feature of the present invention, the cap member is provided with a structure for preventing an emergence of the distal end from the cap member through the aperture in the absence of a longitudinal force on the spring tending to compress the spring. That structure can, for example, define a labyrinthine type path extending to the aperture, whereby the needle can emerge from the aperture only upon application of a predetermined series of directed forces to the cap member. The preventitive structure may alternatively or additionally include a disposition of the aperture in the cap member at a point corresponding to a relatively high potential energy configuration of the spring. In that case, the distal end of the needle is seated in a recess in the cap member, the recess corresponding to a relatively low potential energy of the spring.

According to a supplemental feature of the present invention, an adhesive layer is provided on an outer surface of the cap member for temporarily adhering the cap member to a skin surface of a patient during removal of the distal end of the needle from the patient. This feature serves to ensure that the sharp distal end of the needle is retracted inside the cap member during a withdrawal stroke of the needle.

A syringe is generally fixed to the needle at the proximal end, the syringe communicating with the needle. The spring is thus connected at one end to the syringe and at the opposite end to the cap member.

A hypodermic device comprises, in accordance with another conceptualization of the present invention, a hollow needle having a sharp distal end and a proximal end opposite thereto, a spring connected to the needle, and a cover connected to the spring for covering the distal end of the needle in a low potential configuration of the spring and for enabling an uncovering of the distal end of the needle in a second, relatively high potential configuration of the spring.

The cover may take the form of a cap member provided with an aperture for the controlled emergence of the sharp distal end of the needle. The cap member is connected to one end of the spring which is in turn connected at an opposite end to the needle at the proximal end thereof. More specifically, the spring is a helical spring connected to the proximal end of the needle, while the needle extends longitudinally through the spring.

As discussed hereinabove, the cap member may be provided with means for preventing an emergence of the distal end from the cap member through the aperture in the absence of a longitudinal force on the spring tending to compress the spring. In addition, an adhesive layer is advantageously provided on an outer surface of the cap member for temporarily adhering the cap member to a skin surface of a patient during removal of the distal end of the needle from the patient.

A method for use in obtaining access to an internal organ of a patient comprises, in accordance with the present invention, the step of (a) providing a hypodermic assembly including a hollow needle having a sharp distal end, a proximal end and an aperture, the hypodermic assembly further including a cap member shiftably and essentially permanently attached to the needle so as to cover the distal end in a storage configuration of the hypodermic assembly. Other steps of the method include (b) shifting the cap member relative to the needle to eject the distal end of the needle from the cap member through the aperture, (c) inserting the distal end of the needle through a skin surface of a patient and into an organ of the patient, (d) withdrawing the needle from the patient, (e) maintaining the cap member in contact with the skin surface upon insertion of the distal end of the needle through the skin surface and during the step of withdrawing, and (f) automatically retracting the distal end of the needle back into the cap member upon completion of the step of withdrawing.

Pursuant to another feature of the present invention, where the hypodermic assembly further includes a spring connecting the cap member to the needle, the step of shifting includes the step of deforming the spring. Where the spring is a helical spring surrounding the needle, the step of deforming includes the step of compressing the spring. In that case, the retraction of the needle into the cap member is accomplished by extending the spring.

Where the cap member is provided with a layer of adhesive, maintaining the cap member in contact with the skin surface includes the step of temporarily adhering the cap member to the skin surface during the withdrawal of the needle from the patient.

A hypodermic needle covering in accordance with the present invention greatly reduces the chances that hospital personnel might become inadvertently infected with contagious disease germs from used hypodermic needles. A hypodermic needle covering cannot be misplaced or forgotten because it is attached to the needle. Moreover, covering the needle upon use thereof occurs automatically upon withdrawal of the needle from the patient.

DETAILED DESCRIPTION

Figure 1:
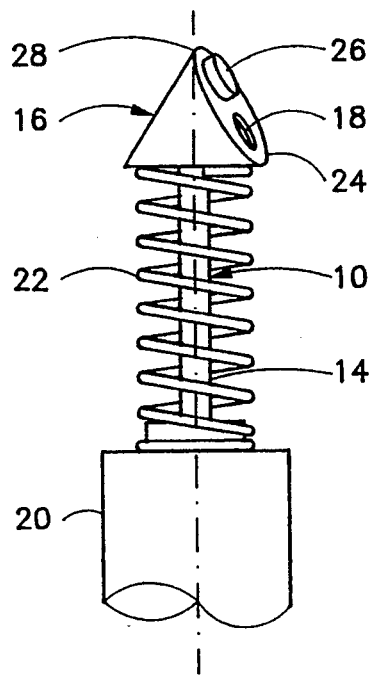
FIG. 1 is a schematic side elevational view of a hypodermic needle with a spring loaded protective cap, in accordance with the present invention, showing the needle assembly in a storage configuration.
Figure 2:
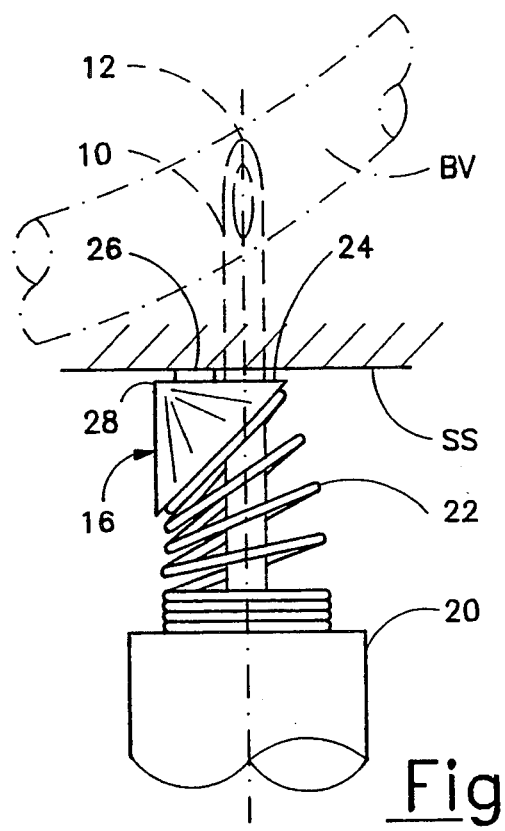
FIG. 2 is a schematic side elevational view, on a larger scale, of the needle assembly of FIG. 1, showing the cap displaced and the needle extended relative thereto in a use configuration of the needle assembly.

As illustrated in FIGS. 1 and 2, a hypodermic needle assembly comprises a hollow needle 10 having a sharp distal end 12 and a proximal end 14 opposite thereto. A safety cap member 16 provided with an eccentrically located aperture 18 is connected to a syringe 20 at the proximal end or base 14 of needle 10 via a helical spring 22. Hypodermic needle 10 is inserted longitudinally through spring 22 so that the spring surrounds the needle and so that cap member 16 covers distal end 12 of needle 10.

Spring 22 thus serves to couple needle 10 and cap member 16 essentially permanently to one another so that the cap member covers distal end 12 of needle 10 in a storage configuration of the needle and cap member 16, as shown in FIG. 1. Spring 22 enables a displacement of cap member 16 relative to needle 10 so that distal end 12 of the needle may be extended from cap member 16 through aperture 18. Spring 22 further functions to return cap member 16 to the storage configuration of FIG. 1 upon removal of distal end 12 of needle 10 from a skin surface SS of a patient following an insertion of the needle through the skin surface and into an underlying organ such as a blood vessel BV.

As illustrated in FIGS. 1 and 2, cap member 16 has an essentially conical shape which is truncated along one side to have a planar surface or face 24. Planar face 24 is provided with an adhesive layer 26 for temporarily adhering cap member 16 to skin surface SS during removal of distal end 12 of needle 10 from the patient. Adhesive layer 26 ensures that distal needle end 12 is retracted automatically inside cap member 16 upon a withdrawal of needle 10 from the patient.

Cap member 16 has a point or apex 28 which receives distal end 12 of needle 10 in the storage configuration of the needle assembly (FIG. 1). Apex 28 corresponds to a low potential energy configuration of spring 22: spring 22 tends to shift cap member 16 relative to needle 10 so that distal end 12 of the needle is seated at apex 28.

Aperture 18 is located in face 24 at an end thereof spaced from apex 28. Aperture 18 is accordingly located at a point corresponding to a relatively high potential energy configuration of spring 22. To eject the distal end 12 of needle 10 from cap member 16 through aperture 18 prior to an intravenous injection or blood sampling operation, cap member 16 must be shiftly longitudinally or axially towards the proximal end 14 of needle 10, thereby compressing spring 22 in opposition to its internal spring constant. In addition, cap member 16 must be shifted laterally so that distal end 12 of needle 10 moves in a radial or lateral direction towards aperture 18.

Upon an emergence of distal end 16 through aperture 18, needle 10 may be inserted through skin surface SS and into blood vessel BV. During this insertion and during subsequent withdrawal of the needle 10 from the patient, cap member 16 is maintained in contact with skin surface SS through the compressive action of helical spring 22 and through the adhesive force exerted by layer 26.

Figure 3:
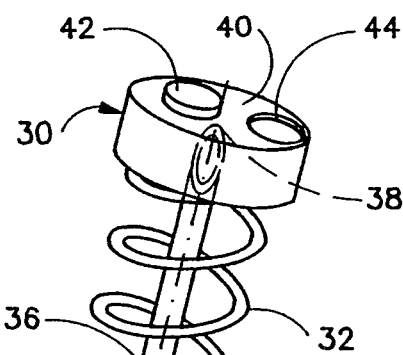
FIG. 3 is a schematic perspective view of another hypodermic needle assembly in accordance with the present invention, showing the needle assembly in a storage configuration.

As illustrated in FIG. 3, another hypodermic needle assembly comprises a cap member 30 attached to the distal end of a helical spring 32 in turn attached at its proximal end to a syringe 34. A hypodermic needle 36 extends from syringe 34 axially through spring 32 so that a sharp distal end or tip 38 of needle 36 is encased or covered by cap member 20 in a storage and transport configuration of the hypodermic needle assembly. Cap member 30 is essentially cylindrical and includes a transverse planar surface 40 provided with an adhesive layer 42 for temporarily adhering cap member 30 to a skin surface during removal of distal tip 38 of needle 36 from a patient. Adhesive layer 42 ensures that needle tip 38 is retracted automatically and immediately inside cap member 30 upon a withdrawal of needle 36 from the patient. An aperture 44 is provided in transverse surface 40 of cap member 30 for ejection of needle 36 from cap member 30 prior to insertion of the needle into a patient.

Figure 4:
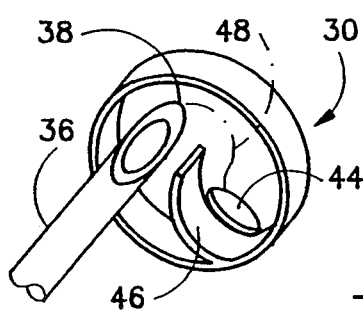
FIG. 4 is a schematic perspective bottom view of a protective or safety cap member in the needle assembly embodiment of FIG. 3.

As depicted in FIG. 4, the underside of cap member 30 is provided with an irregular projection 46 defining a labyrinthine type path 48 extending to aperture 44, whereby needle 36 can emerge from cap member 30 through aperture 46 only upon application of a predetermined series of directed forces to the cap member.

Figure 5:
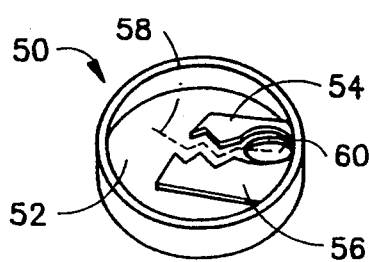
FIG. 5 is a schematic perspective view of another protective or safety cap member for incorporation in the needle assembly embodiment of FIG. 3.

FIG. 5 illustrates an alternative cap member 50 for use in the hypodermic needle assembly of FIG. 3. Cap member 50 is provided along an inner transverse end surface 52 with a pair of sawtooth type projections 54 and 56 which together define a labyrinthine type path 58 extending to an aperture 60 in the end surface 52. A needle can be ejected from cap member 50 through aperture 60 only upon application of a predetermined series of directed forces to the cap member.

Figure 6:
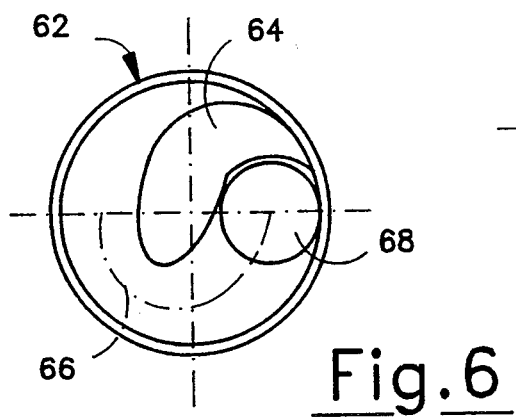
FIG. 6 is a schematic bottom view of yet another protective or safety cap member for incorporation in the needle assembly embodiment of FIG. 3.

FIG. 6 shows yet another cap member 62 with an internally located projection 64 defining a labyrinthine path 66 extending to an aperture 68.

Figure 7:
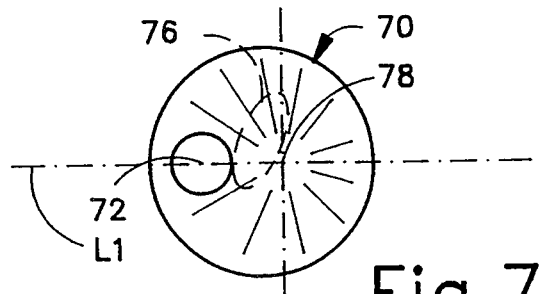
FIG. 7 is a top view of another protective or safety cap member utilizable in the needle assembly embodiment of FIGS. 1 and 2.
Figure 8:
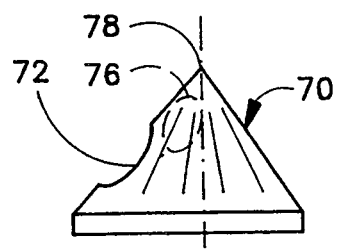
FIG. 8 is a side elevational view of the cap member of FIG. 7.
Figure 9:
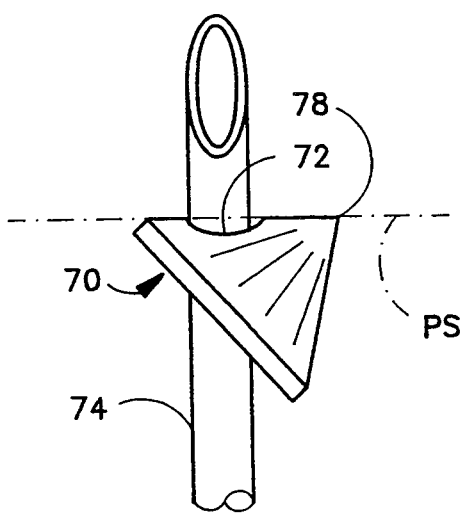
FIG. 9 is a side elevational view of the cap member of FIGS. 7 and 8, showing use of that cap member with a hypodermic needle.

As shown in FIGS. 7-9, another protective or safety cap 70 for a hypodermic needle assembly has an eccentric conical shape and is provided with an eccentric aperture 72 which is traversed by a hypodermic needle 74 during use of the needle assembly. A layer of adhesive 76 may be provided on cap 70 between aperture 72 and an apex 78 of cap 70. During insertion of needle 74 through a patient's skin surface PS, cap member lies against the skin surface along a line L1 defined by aperture 72 and apex 78.

Figure 10:
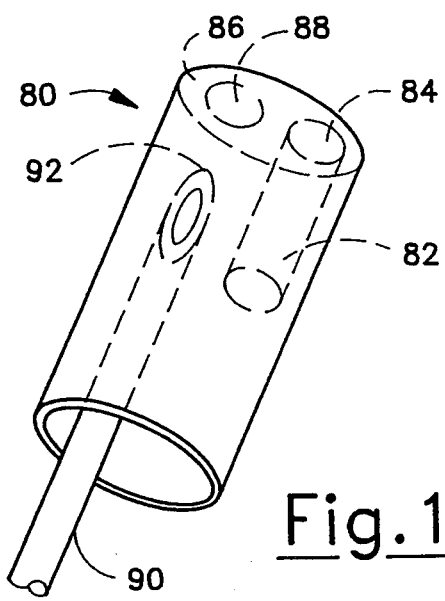
FIG. 10 is a schematic perspective view of yet another cap member utilizable in a hypodermic needle assembly in accordance with the present invention.

FIG. 10 depicts yet another cap member 80 for use in an automatic capping hypodermic needle assembly. Cap member 80 is cylindrical and includes a longitudinally extending cylindrical sleeve 82 leading to an aperture 84 in a distal end wall 86 of the cap. An adhesive layer 88 is provided on the end wall 86 for holding cap member 80 to a patient's skin surface during a withdrawal of a needle 90 so that a distal end 92 of the needle passes through aperture 84 and sleeve 82 and assumes a storage position, as shown.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A hypodermic device comprising:

a hollow needle having a sharp distal end and a proximal end opposite thereto;

a spring connected to said needle;

cover means connected to said spring for covering said distal end of said needle in a low potential configuration of said spring and for enabling an uncovering of said distal end of said needle in a second, relatively high potential configuration of said spring, said cover means including a cap member provided with an aperture, said cap member being connected to said needle via said spring, said cap member being fixed to said spring; and an adhesive layer on an outer surface of said cap member for temporarily adhering said cap member to a skin surface of a patient during removal of said distal end of said needle from the patient.

2. The device defined in claim 1 wherein said cap member is fixed to one end of said spring, said spring being connected at an opposite end to said needle at said proximal end thereof.

3. The device defined in claim 2 wherein said spring is a helical spring connected at said opposite end to said proximal end of said needle, said needle extending longitudinally through said spring.

4. The device defined in claim 3 wherein said cap member is provided with means for preventing an emergence of said distal end from said cap member through said aperture in the absence of a longitudinal force on said spring tending to compress said spring.

5. The device defined in claim 2 wherein said spring is connected at said opposite end to said proximal end of said needle via a syringe element.

6. A method for use in obtaining access to an internal organ of a patient, comprising the steps of:

providing a hypodermic assembly including a hollow needle having a sharp distal end and a proximal end, said hypodermic assembly further including a cap member shiftably and essentially permanently attached to said needle so as to cover said distal end in a storage configuration of said hypodermic assembly, said cap member being provided with an eccentrically disposed aperture laterally spaced from said sharp distal end of said needle in said storage configuration of said hypodermic assembly;

shifting said cap member initially laterally relative to said needle to align said sharp distal end with said aperture and subsequently longitudinally relative to said needle to eject said distal end of said needle from said cap member through said aperture;

inserting said distal end of said needle through a skin surface of a patient and into an organ of the patient;

withdrawing said needle from the patient;

maintaining said cap member in contact with said skin surface upon insertion of said distal end Of said needle through said skin surface end during said step of withdrawing; and automatically retracting said distal end of said needle back into said cap member upon completion of said step of withdrawing.

7. The method defined in claim 6 wherein said hypodermic assembly further includes a spring connecting said cap member to said needle, said step of shifting including the step of deforming said spring.

8. The method defined in claim 7 wherein said spring is a helical spring surrounding said needle, said step of deforming including the step of compressing said spring.

9. The method defined in claim 8 wherein said step of retracting includes the step of extending said spring.

10. The method defined in claim 6 wherein said cap member is provided with a layer of adhesive, said step of maintaining including the step of temporarily adhering said cap member to said skin surface during said step of withdrawing.

11. A hypodermic access method comprising the steps of:

providing a hollow needle having a sharp distal end and a proximal end opposite thereto, a safety cap member provided with an aperture being permanently connected to said needle via a spring;

in a pre-utilization storage configuration of said needle and said cap member, maintaining said sharp distal end of said needle covered with said cap and laterally spaced from said aperture;

displacing said cap member initially laterally relative to said needle to align said sharp distal end with said aperture and subsequently longitudinally relative to said needle to extend said sharp distal end of said needle through said aperture, said step of displacing including the step of deforming said spring;

upon extension of said sharp distal end of said needle through said aperture, inserting said distal end of said needle through a skin surface of a patient and into an organ of the patient;

withdrawing said needle from the patient; and upon withdrawal of said needle from the patient, automatically shifting said cap back to cover said sharp distal end of said needle and return said cap member to said storage configuration relative to said needle, said step of automatically shifting being implemented by converting potential energy stored in said spring during said step of deforming.

12. The method defined in claim 11, further comprising the step of maintaining said cap member in engagement with the patient during at least a portion of each of said steps of inserting and withdrawing.

13. The method defined in claim 11, further comprising the step of temporarily adhering an outer surface of said cap member to the patient upon insertion of said needle into the patient and during withdrawal of said distal end of said needle from the patient.

14. The method defined in claim 11 wherein said spring is a helical spring connected at one end to said proximal end of said needle, said needle extending longitudinally through said spring, said step of deforming including the step of compressing said spring.

15. A hypodermic access method comprising the steps of:

providing a hollow needle having a sharp distal end and a proximal end opposite thereto, a safety cap member provided with an aperture being permanently connected to said needle via a helical spring, said needle passing through said sprang;

in a pre-utilization storage configuration of said needle and said cap member, maintaining said sharp distal end of said needle covered with said cap and laterally spaced from said aperture;

displacing said cap member initially laterally relative to said needle to align said sharp distal end with said aperture and subsequently longitudinally relative to said needle to extend said sharp distal end of said needle through said aperture, said step of displacing including the step of compressing said spring;

upon displacement of said cap member relative to said needle, extending said sharp distal end of said needle from said cap member through said aperture;

inserting said distal end of said needle through a skin surface of a patient and into an organ of the patient;

withdrawing said needle from the patient; and returning said cap member to said storage configuration relative to said needle upon withdrawal of said distal end of said needle from the patient, said step of returning including the step of relaxing or releasing said spring from a compressed configuration.

16. The method defined in claim 15, further comprising the step of maintaining said cap member in engagement with the patient during at least a portion of each of said steps of inserting and withdrawing.

17. The method defined in claim 15, further comprising the step of temporarily adhering an outer surface of said cap member to the patient upon insertion of said needle into the patient and during withdrawal of said distal end of said needle from the patient.

* * * * *

UNITED STATES PATENT AND TRADEMARK OFFICE
CERTIFICATE OF CORRECTION

PATENT NO. : 5,364,370
DATED : November 15, 1994
INVENTOR(S) : Gregg M. Szerlip and Peter J. Wilk It is certified that error appears in the above-indentified patent and that said Letters Patent is hereby corrected as shown below:

Column 4, line 54, change "shiftly" to --shifted--.

Column 5, line 23, change "46" to --44--; line 44, change "cap member" to --cap 70--.

Column 6, line 55, claim 6, change "Of" to --of--.

Column 8, line 12, claim 15, change "sprang" to --spring--.

Signed and Sealed this

Twenty-third Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,364,370
DATED : November 15, 1994
INVENTOR(S) : Gregg M. Szerlip and Peter J. Wilk It is certified that error appears in the above-identified patent and that said Letters Patent is hereby corrected as shown below:

On the title page item [54], and column 1, line 1, change "HYPRODERMIC" to --HYPODERMIC--

Signed and Sealed this

Nineteenth Day of December, 2000

Attest:

Q. TODD DICKINSON

*Attesting Officer*      *Commissioner of Patents and Trademarks*